United States Patent
Flexman et al.

(10) Patent No.: US 11,191,593 B2
(45) Date of Patent: Dec. 7, 2021

(54) TRIGGERING WITH OPTICAL SHAPE SENSING FIBER

(71) Applicant: KONINKLIJKE PHILIPS N.V., Eindhoven (NL)

(72) Inventors: Molly Lara Flexman, Melrose, MA (US); Aryeh Leib Reinstein, Bronx, NY (US); Xingchi He, Columbia, MD (US); Paul Thienphrapa, Cambridge, MA (US); Dirk Dijkkamp, Waalre (NL); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1245 days.

(21) Appl. No.: 15/514,619

(22) PCT Filed: Sep. 16, 2015

(86) PCT No.: PCT/IB2015/057111
§ 371 (c)(1),
(2) Date: Mar. 27, 2017

(87) PCT Pub. No.: WO2016/051302
PCT Pub. Date: Apr. 7, 2016

(65) Prior Publication Data
US 2017/0215973 A1 Aug. 3, 2017

Related U.S. Application Data

(60) Provisional application No. 62/057,281, filed on Sep. 30, 2014.

(51) Int. Cl.
*A61B 34/20* (2016.01)
*G01B 11/24* (2006.01)
(Continued)

(52) U.S. Cl.
CPC .............. *A61B 34/20* (2016.02); *G01B 11/24* (2013.01); *G01D 5/35358* (2013.01);
(Continued)

(58) Field of Classification Search
CPC ...... A61B 2034/2061; A61B 2090/364; A61B 2090/365; A61B 34/20; A61B 34/30;
(Continued)

(56) References Cited

U.S. PATENT DOCUMENTS 8,182,433 B2  5/2012  Leo
8,896,847 B2  11/2014  Vincent et al.
(Continued)

FOREIGN PATENT DOCUMENTS

JP  S60163311  8/1985
JP  2005338361  12/2005
(Continued)

*Primary Examiner* — Baisakhi Roy

(57) ABSTRACT

A triggering device includes an optical fiber (126) configured for optical shape sensing. A supporting element (104) is configured to support a portion of the optical fiber. An interface element (106) is configured to interact with the optical fiber associated with the supporting element to cause a change in a property of the fiber. A sensing module (115) is configured to interpret an optical signal to determine changes in the property of the fiber and accordingly generate a corresponding trigger signal.

20 Claims, 13 Drawing Sheets

(51) Int. Cl.
    *G01D 5/353*     (2006.01)
    *A61B 90/00*     (2016.01)

(52) U.S. Cl.
    CPC . *A61B 2034/2061* (2016.02); *A61B 2090/364* (2016.02); *A61B 2090/365* (2016.02)

(58) Field of Classification Search
    CPC ........ A61B 2090/064; A61B 2090/065; A61B 1/00045; A61B 1/0042; A61B 1/0055; A61B 1/05
    See application file for complete search history.

(56) References Cited

U.S. PATENT DOCUMENTS

| | | | |
|---|---|---|---|
| 9,285,246 B2 | 3/2016 | Prisco et al. | |
| 9,737,198 B2* | 8/2017 | Laby | A61B 1/00045 |
| 10,228,556 B2* | 3/2019 | Reddy | G02B 6/0288 |
| 2004/0163809 A1 | 8/2004 | Mayeu et al. | |
| 2007/0193362 A1 | 8/2007 | Ferguson | |
| 2009/0137952 A1* | 5/2009 | Ramamurthy | A61B 5/4887 604/95.01 |
| 2009/0177095 A1 | 7/2009 | Aeby | |
| 2013/0204072 A1* | 8/2013 | Verard | A61B 8/483 600/8 |
| 2015/0285626 A1* | 10/2015 | Yamauchi | G01L 1/242 356/32 |
| 2015/0342695 A1* | 12/2015 | He | G01L 1/246 606/130 |
| 2016/0008026 A1* | 1/2016 | Elayaperumal | G01L 1/246 600/424 |
| 2016/0228200 A1 | 8/2016 | Denissen et al. | |

FOREIGN PATENT DOCUMENTS

| | | |
|---|---|---|
| WO | 2011/060225 | 5/2011 |
| WO | 2013168056 | 11/2013 |

* cited by examiner

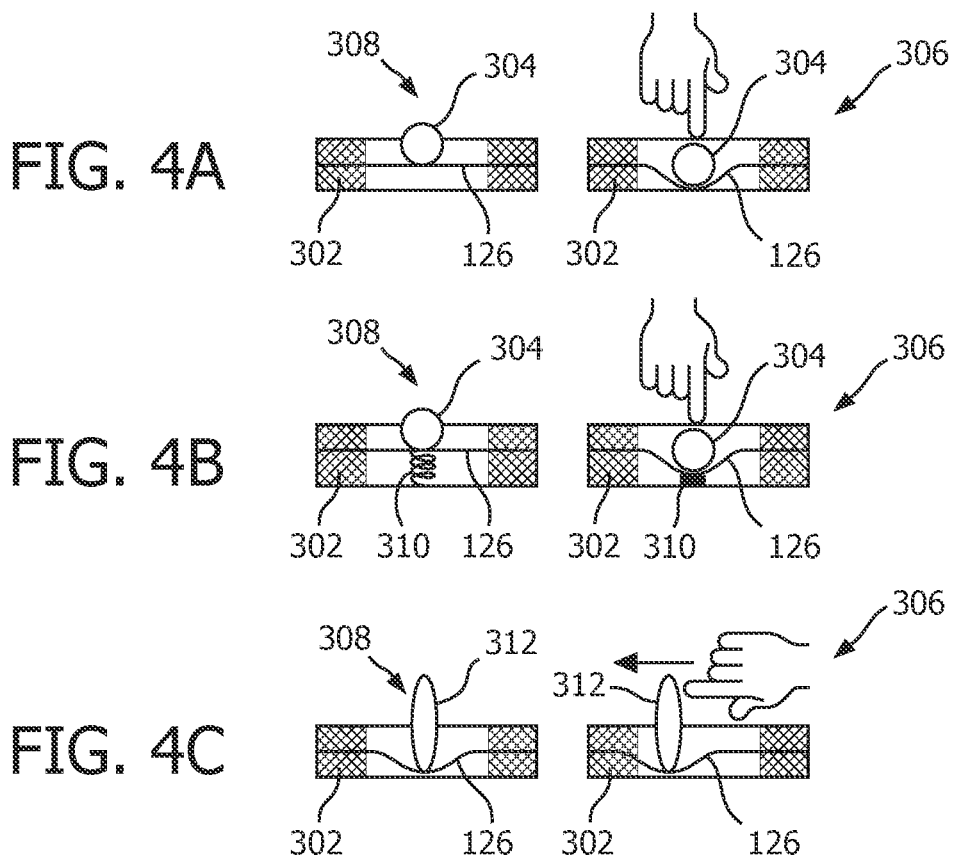
FIG. 4A
FIG. 4B
FIG. 4C
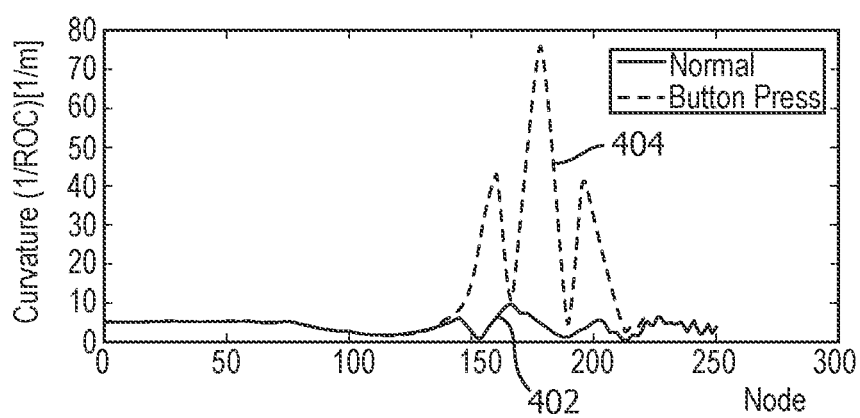
FIG. 5

TRIGGERING WITH OPTICAL SHAPE SENSING FIBER

CROSS-REFERENCE TO PRIOR APPLICATIONS

This application is the U.S. National Phase application under 35 U.S.C. § 371 of International Application Serial No. PCT/IB2015/057111, filed on Sep. 16, 2015, which claims the benefit of U.S. Application Ser. No. 62/057,281, filed on Sep. 30, 2014. These applications are hereby incorporated by reference herein.

BACKGROUND

Technical Field

This disclosure relates to medical instruments and more particularly to shape sensing optical fibers for triggering events in medical and other applications.

Description of the Related Art

Optical shape sensing (OSS) uses reflected light along one or more optical fibers to reconstruct a shape. A principle involved makes use of distributed strain measurement in the optical fiber using characteristic Rayleigh backscatter or controlled grating patterns. The shape along the optical fiber begins at a specific point along the sensor, known as the launch point, home or zero position, and the subsequent shape position and orientation are relative to that point. Implementations of such optical fibers may be about 200 microns in diameter and can be up to a few meters long while maintaining millimeter level accuracy Optical shape sensing fibers can be integrated into a wide range of medical devices to provide live guidance medical procedures. As an example, a guidewire and catheter may be employed for navigation in a blood vessel with the optical shape sensing measurement overlaid upon a pre-operative computed tomography (CT) image.

Computer assisted surgery (CAS) provides live navigational guidance during surgical interventions such as neuro, spine, and orthopedic procedures. Key orthopedic procedures that use this technology include knee replacement, hip replacement and anterior cruciate ligament (ACL) repair. One benefit provided by CAS is live guidance as to optimal positioning of replacement implants as well as improved intraoperative verification of joint biomechanics. In a CAS procedure, registration of the bone or anatomy of interest is necessary to provide a common tracking coordinate system. In such a procedure, a clinician holds a tip of a tracked pointer to certain landmarks on the anatomy (for example, bony landmarks such as ridges) and indicates to a software system when the pointer is in the designated position. Once a series of landmarks are acquired in this fashion, the user may also run the pointer over the surface, painting the anatomy and digitizing the surface into the tracking coordinate frame. These points can be used to build a model of the anatomy, to morph an existing model, or to register to pre-operative or intra-operative imaging.

There are multiple applications for a user to indicate when they have positioned a medical instrument in a specific position or orientation. For example, during registration for computer aided surgery in orthopaedics, the clinician holds a pointer to a specific bony landmark and then triggers the acquisition of that position with a mouse click. This requires the use of two hands or two operators, neither of which is ideal for workflow. Having a mouse within the surgical area is also not ideal for maintaining a sterile environment.

In vascular navigation, it is typical for the operator to position targets or rings at important positions during a procedure. These can serve as notable points to be returned to at various stages of the procedure. In a shape-sensed catheter or guidewire, these target shapes or points may be stored when triggered by the user.

SUMMARY

In accordance with the present principles, a triggering device includes an optical fiber configured for optical shape sensing. A supporting element is configured to support a portion of the optical fiber. An interface element is configured to interact with the optical fiber associated with the supporting element to cause a change in a property of the fiber. A sensing module is configured to interpret an optical signal to determine changes in the property of the fiber and accordingly generate a corresponding trigger signal.

A triggering system includes one or more optical fibers configured for optical shape sensing and a medical instrument including the one or more optical fibers. The medical instrument is tracked by optical shape sensing, and the medical instrument forms a supporting device configured to support at least a portion of the one or more optical fibers. An interface element is configured to interface with the one or more optical fibers in the supporting device to cause a change in a property of the one or more optical fibers. A sensing module is configured to interpret an optical signal to determine changes in the property of the fiber and accordingly generate a trigger signal if the given amount is reached.

A method for triggering an event includes supporting at least a portion of an optical fiber in a supporting device; interfacing with the optical fiber in the supporting device to cause a change in a property of the fiber; interpreting an optical signal to determine the change in the property of the optical fiber and triggering an event when the property changes by a given amount.

A change in curvature or shape in a certain region of the fiber is used as an input or trigger to software. However, in order for the triggering to work, an algorithm is used to monitor a specific region of the fiber. This is practical in some cases, where the fiber is integrated into a device such as a catheter. In other cases, however, the trigger region in the fiber may not be fixed. For example, if it is desired to enable a clicker that can slide over the top of a guidewire, then a way is needed to restrict the search region to only the region of the slideable interface element, hub or other fixture in order to identify the trigger. Otherwise, there may be so much change in curvature along the entire fiber during use that it not be possible to pick out the trigger from that signal. It is advantageous to limit the search region, when looking for a specific shape event. Alternatively, it can also be useful to segment the shape into clinically meaningful sections.

Thus, in accordance with the present invention, a template-based search restriction maybe used to segment sensor data and identify the segments that are relevant to a given search. A template-based search restriction can be applied in multiple ways, including, but not limited to: (1) using a hub template to only search within that template for a triggering curvature signal, (2) using an anatomical template to select a portion of the shape, and (3) detecting a template in order to segment the shape into in-body and out-of-body segments. The template may be any characteristic that can be used to correspond to an identifiable, determinable spatial relationship of the sensor data to a deployed sensor optical fiber, such as a characteristic curvature, shape, stress, temperature or other physical property assumed by a point, segment, length or portion of the optical fiber.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIG. 4A is a cross-sectional view of a triggering device showing a normal state and a triggered state using a curvature-inducing button in accordance with one embodiment;

FIG. 4B is a cross-sectional view of a triggering device showing a normal state and a triggered state using a biased button in accordance with one embodiment;

FIG. 4C is a cross-sectional view of a triggering device showing a normal state and a triggered state using a sliding button in accordance with one embodiment;

FIG. 5 is a graph showing curvature (1/m) versus node number for a normal state and a triggered state using an optical fiber in accordance with one embodiment;

DETAILED DESCRIPTION OF EMBODIMENTS

Figure 1:
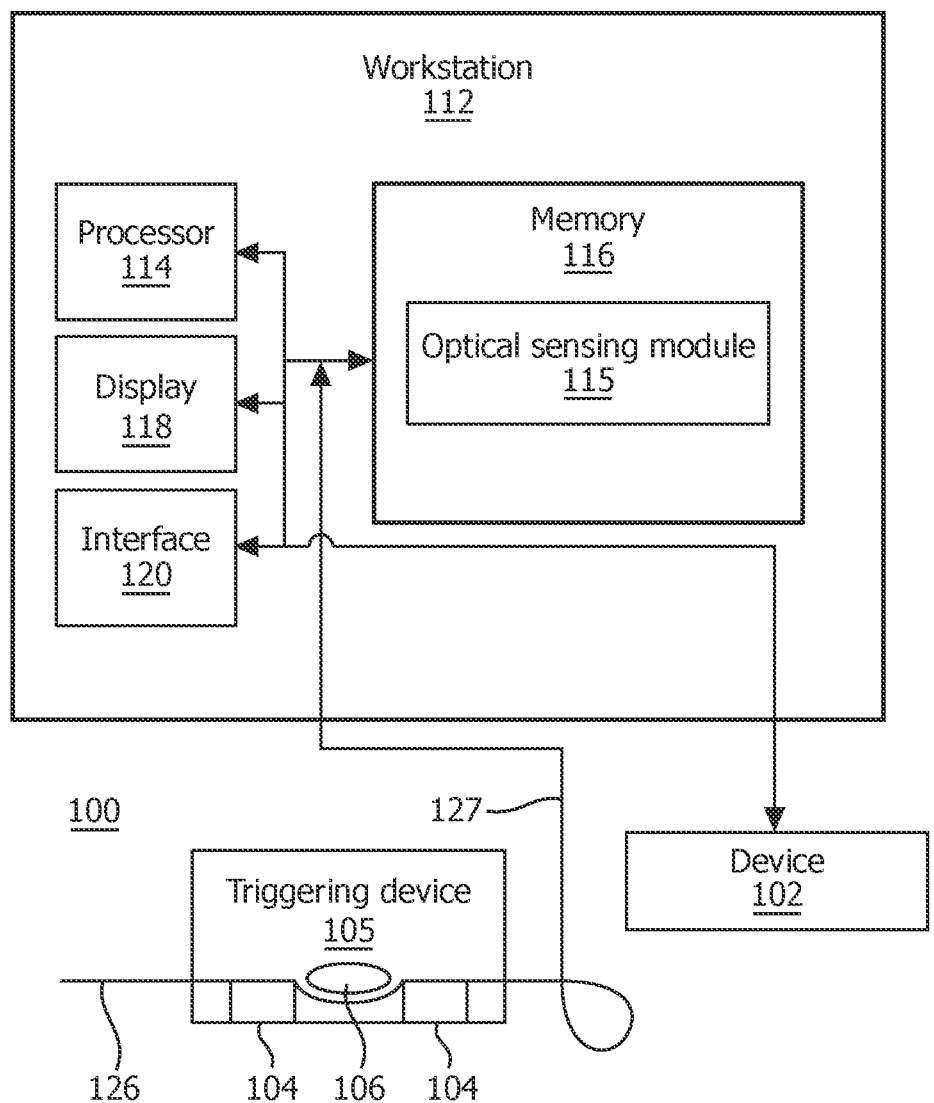
FIG. 1 is a block/flow diagram showing a triggering device including a shape sensing optical fiber in accordance with one embodiment.

In accordance with the present principles, systems and methods are provided for triggering events by employing a shape sensing optical fiber. In particularly useful embodiments, the shape sensing optical fiber is employed to indicate when a medical instrument is positioned in a specific location or orientation. The optical shape sensing fiber can be used as a trigger to provide user input. If an optical shape sensing fiber is already embedded or attached to the medical instrument for tracking a shape or position of the instrument, the present principles provide a sensor that can be used to capture user commands. This may be performed in a plurality of ways. For example, identifying a change in curvature at a defined location along the sensor; matching a specific shape or pattern made with the sensor at a location along the sensor; searching for a change in axial strain or temperature at a location along the sensor, measuring the force between a shape-sensed medical device and another object, etc. Changes in the fiber may be considered as a shape change (e.g., curvature, shape, twist, orientation, etc.) or a change in axial strain (e.g., due to temperature, tension, etc.).

Adding extra devices, such as wires and buttons to a medical device can be expensive and awkward in many instances. Using the optical fiber of a shape sensing system, which is already embedded into the device solves both of these issues with minimal cost and/or minimal or no changes to the device profile. The optical fiber can be employed as a user input device, e.g., a switch, trigger, control, etc. In addition, the optical fiber has no interaction or effect on its surrounding environment, making it especially suitable for use with magnetic resonance imaging (MRI) or other imaging or medical instrumentalities.

It should be understood that the present invention will be described in terms of medical instruments; however, the teachings of the present invention are much broader and are applicable to any instruments, which may benefit from the use of a shape sensing optical fiber triggering system. In some embodiments, the present principles are employed with or in devices for tracking and/or analyzing complex biological or mechanical systems. In particular, the present principles are applicable to devices and procedures for biological systems, procedures in all areas of the body, such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for creating a triggering signal using shape sensing optical fiber triggering is illustratively shown in accordance with one embodiment. System 100 may include a console 112 from which shape sensing signals are interpreted. System 100 may be the system being triggered or may connect with a system, function (e.g., software function) or device 102 to be triggered. By way of example, a mouse click is a triggered event. In particularly useful embodiments, the present principles may be employed to replace a mouse or other form of triggering device. It should be understood that while the present principles describe the use of optical shape sensing, other shape sensing technologies or other optical fiber configurations are also contemplated in accordance with the present principles.

Console 112 preferably includes one or more processors 114 and memory 116 for storing programs and applications. Memory 116 may store an optical sensing module 115 that stores instructions, which when executed by processor 114, cause the processor to interpret optical feedback signals from a shape sensing device or system. Optical sensing module 115 is configured to use the optical signal feedback (and any other feedback) to reconstruct deformations, deflections and other changes associated with a shape sensing optical fiber 126 in a triggering device 105. The triggering device 105 may include any mechanical feature capable of changing a shape, orientation or force on the shape sensing optical fiber 126. In one embodiment, the triggering device 105 includes a supporting element 104 configured to secure the shape sensing optical fiber 126 and a mechanical element or interface element 106 configured to apply a displacement, twist or force to the shape sensing optical fiber 126.

The shape sensing optical fiber 126 of a shape sensing system may be included in, on or through triggering device 105. The shape sensing optical fiber or fibers 126 of the shape sensing system may be coupled to or through the triggering device 105 in a set pattern or patterns. The shape sensing optical fibers 126 connect to the console 112 through cabling 127. The cabling 127 may include fiber optics, electrical connections, other instrumentation, etc., as needed.

The shape sensing optical fiber 126 of the shape sensing system may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. For example, incorporating three or more cores with various sensors (gauges) along the length of a fiber that is embedded in a structure permits a three-dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined. An OSS shape sensor may generate data from thousands of nodes (e.g. individual fiber optic Bragg gratings or distortions causing Rayleigh backscatter). It can be difficult to robustly search through data from along the entire sensor for specific shapes.

It should be noted that other configurations for shape sensing fiber or fibers may be employed and are included within the present principles.

As one alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed. Other embodiments may include different numbers of fibers configured in different structures or configurations.

In one embodiment, console 112 may include a display 118 to permit a user to interact with the console 112 and its components and functions, or any other element within the system 100. This is further facilitated by an interface 120 which may include a keyboard, a mouse, a joystick, a haptic device, or any other peripheral or control to permit user feedback from and interaction with the console 112.

In particularly useful embodiments, a change in an optical signal of the shape sensing optical fiber 126 may be interpreted as a trigger event. The optical signal may include characteristics (e.g., axial strain, shape change, etc.) that are compared to an expected response to indicate that the change is indeed consistent with an expected trigger signal. Once the trigger signal is determined to be such by optical sensing module 115, an event is initiated. The event may include activating/deactivating the function or device 102 (powering on/off or changing its function), activating/deactivating a software function (102 or 115), providing confirmation of the presence of a user, testing the shape sensing system, etc. The triggering device 105 may also be employed to itself provide an initiation signal upon any change in the optical signal to optical sensing module 115 or directly to the function or device 102. In one embodiment, the triggering device 105 may be employed as a security instrument where gesture type and order may be employed to indicate the identity of a particular user. In other embodiments, the triggering device 105 acts as an enabling feature to initiate operations of the function or device 102. It should be understood that the function or device 102 and triggering device 105 may be integrated into a same instrument or assembly. In addition, multiple triggering devices 105 and/or multiple functions or devices 102 may be employed in any combination.

A trigger of the triggering device 105 can be generated using the shape sensing optical fiber 126 to respond to one or more changes. The changes may include, e.g., a curvature change, a thermal change (or a change in axial strain), a shape change, etc. These inputs can be used separately, in combination, and at one or more points along the shape sensing optical fiber 126. In one embodiment, a curvature change is employed to cause an action in software, e.g., optical sensing module 115. The supporting element 104 may include a mechanical element, fingers of a user, a portion of a medical device (e.g., a catheter, etc.), or any other supporting fixture, surface or material. The interface element 106 may also include a mechanical element, a finger of the user, a portion of a medical device, etc. The supporting element 104 and the interface element 106 work together to implement curvature changes in shape sensing optical fiber 126. In one example, a catheter or other device that includes the shape sensing optical fiber 126 may have a firm portion (supporting elements 104) and a soft portion (interface element 106). When the soft portion is depressed relative to the firm portion, a curvature in the shape sensing optical fiber 126 is produced that can cause the trigger signal or triggering event. In another example, the interface element 106 may include an actuator or other automatically controlled mechanism.

Figure 2A:
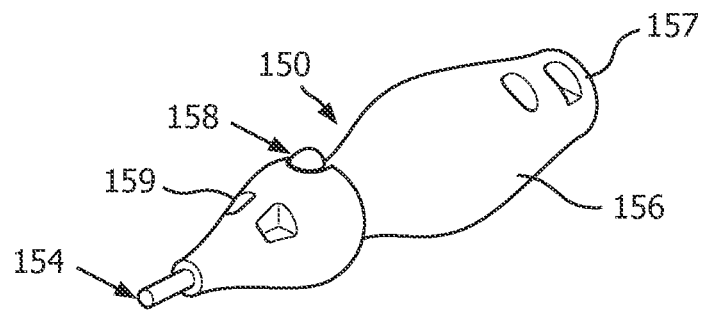
FIG. 2A is a perspective view of a pointer device including a triggering function in accordance with the present principles.
Figure 2B:
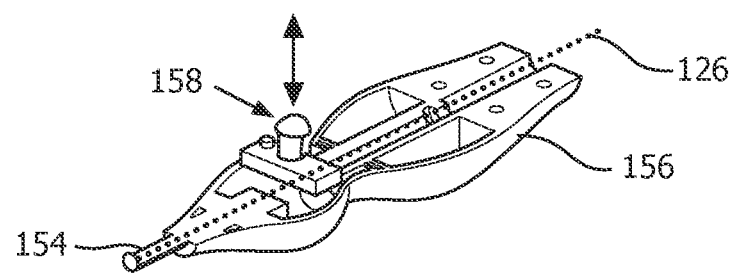
FIG. 2B is a perspective view of the pointer device of FIG. 2A having covers removed to show an optical fiber in a normal state in accordance with the present principles.
Figure 2C:
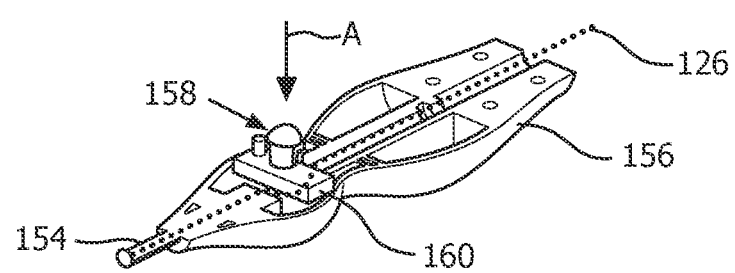
FIG. 2C is a perspective view of the pointer device of FIG. 2A having covers removed to show an optical fiber in a curved or triggered state in accordance with the present principles.

Referring to FIGS. 2A-2C, diagrams showing a pointing device 150 including a shape sensing optical fiber 126 is shown in accordance with one embodiment. In FIG. 2A, the pointing device 150 includes a handle 156 and depicts a cover 157 attached thereto to protect the shape sensing optical fiber 126 (FIG. 2B). A fiber tip 154 is employed to locate a position on a bone or other position or location. When the fiber tip 154 is positioned, the user can depress a spring returned button 158 (interface element) to record the position of the pointing device 150. The position of the pointing device 150 is known from the shape sensing optical fiber 126 or by other means. In this way, a surface in contact with the pointing device 150 can be digitized. A cover 159 may be employed to clamp a distal portion of the shape sensing optical fiber 126 to avoid tip motion.

In FIG. 2B, the covers 157 and 159 are shown removed to visualize the shape sensing optical fiber 126. The fiber is supported by the handle 156 (e.g., supporting element) and is shown in its normal (not curved) state. In FIG. 2C, the spring returned button 158 is depressed in the direction of arrow "A" to induce a curvature 160 in the shape sensing optical fiber 126. This curvature 160 triggers a storage function to store the tip position in memory.

Figure 3A:
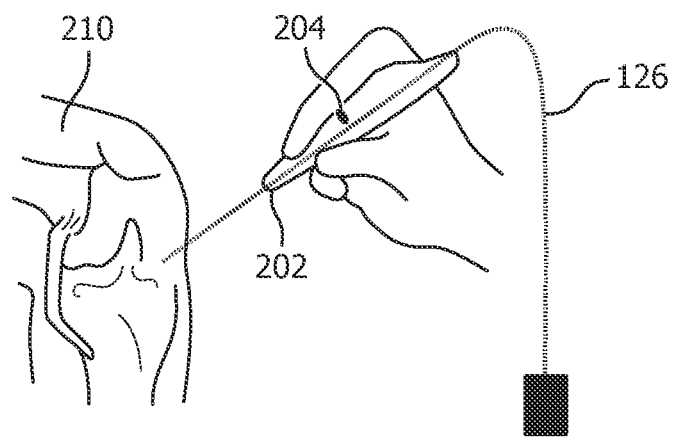
FIG. 3A is a diagram showing a triggering device built into a medical instrument including a shape sensing optical fiber in a normal or neutral state in accordance with one embodiment.
Figure 3B:
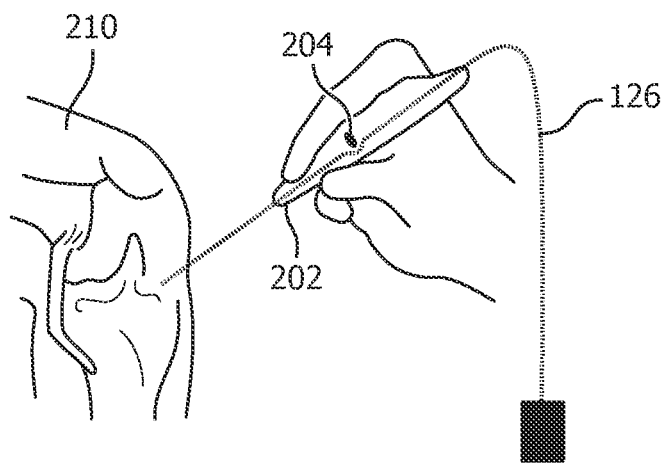
FIG. 3B is a diagram showing a triggering device built into a medical instrument including a shape sensing optical fiber deflected into a trigger state in accordance with one embodiment.
Figure 3C:
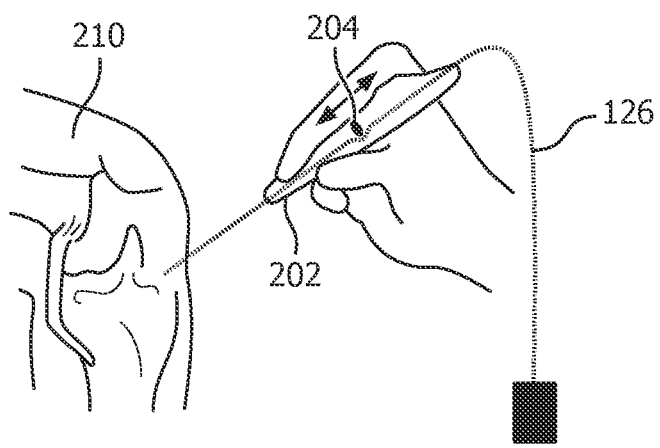
FIG. 3C is a diagram showing a triggering device built into a medical instrument including a shape sensing optical fiber deflected with a sliding button into a trigger state in accordance with one embodiment.

Referring to FIGS. 3A-3C, a medical instrument 202 (or pointing device 150) is shown relative to a knee 210 during an orthopedic procedure. A shape sensing optical fiber 126 is shown in its neutral or normal state within the medical instrument 202 in FIG. 3A. In the embodiment depicted, the medical instrument 202 includes an orthopedic pointer with a push button 204 or sliding button 206 integrated into a handle of the pointing device. When the push button 204 or sliding button 206 are moved or depressed, the curvature of the shape sensing optical fiber 126 changes. This could similarly be accomplished with a clip-on attachment (externally) to the pointing device or the like.

The shape sensing optical fiber 126 is configured to deform in curvature when a push button 204 is pressed as shown in FIG. 3B. In this embodiment, the supporting element 104 (FIG. 1) includes the medical instrument 202, and the interface element 106 (FIG. 1) includes the push button 204. In FIG. 3C, the sliding button 206 provides a pressed state translatable over a length of the shape sensing optical fiber 126. Shape sensing optical fiber 126 may be embedded into the medical instrument 202 to measure its shape, position and orientation. The same shape sensing optical fiber 126 can also be used for user input. The shape sensing optical fiber 126 may be employed in any instrument, and is not limited to medical devices.

Referring to FIGS. 4A-4C, different illustrative configurations are depicted showing normal states and displaced states for a plurality of illustrative triggering device configurations in accordance with the present principles. In FIG. 4A, the shape sensing optical fiber 126 is configured to include a supporting device or instrument 302 to change in curvature during a press of a button 304. A trigger state 306 is achieved by moving the shape sensing optical fiber 126 from a normal position (unpressed) state 308. FIG. 4B shows the button 304 and shape sensing optical fiber 126 biased by a biasing element 310 to ensure that they return to the normal position 308 when not being pressed in the trigger state 306. Other biasing elements may also be employed. In FIG. 4C, an alternative motion includes a sliding button 312, which can translate a curvature along the shape sensing optical fiber 126.

FIGS. 4A-4C show how the shape sensing optical fiber 126 can be configured to generate a change in curvature when the button 304 or sliding button 312 is pressed or moved. This push button 304, or sliding button 312 can be placed anywhere along the shape sensing optical fiber 126 after a launch point. For example, push button 304, or sliding button 312 can be within a handle of the instrument (as shown in FIG. 3A-3C) or within a catheter hub.

When the push button 304, or sliding button 312 is pressed or moved, the shape sensing optical fiber 126 (bare or within a protective tube) is deflected by the push button 304, or sliding button 312 or by a connecting device such as a plunger or the like. This causes a change in curvature from very low curvature in its normal (straight) shape, to a higher curvature in the activated state. Biasing elements 310 can be included to ensure that the shape sensing optical fiber 126 always returns to its normal, straight, configuration when not being depressed. Alternatively, the curvature can always be present in the fiber, but translated along the fiber to provide not only an on/off capability, but also a potentiometer functionality (the ability to give the user a gradual control), e.g., FIG. 4C.

The above examples describe one-dimensional button motions. The implementations may be further expanded to incorporate additional dimensions. For example, it may be possible to move the button in a similar manner to a thumbstick or a manual gearstick lever on a car and detect the position based on the changes in curvature and/or position. This would expand the functionality beyond a click detector and allow navigation through menus or to switch modes, etc.

Multiple buttons and switches can be included along the function or device 102 to provide rich input functionality. Individual buttons may correspond to different functionality or can change the meaning of other buttons. In addition, one button can be used to detect the connectivity of the device against a dock, while another button can be used as a safety feature, wherein the push button 304, or sliding button 312 needs to be switched or held to enable the functionalities tied to the other buttons.

Other uses of the shape sensing optical fiber 126 as an input device may include integrating the shape sensing optical fiber 126 into a handle or joystick, whose sensed position and orientation is used to guide virtual objects onscreen, such as views of 3D anatomy.

Referring to FIG. 5, a graph of curvature (1/radius of curvature) (1/m) versus node number along a length of fiber is illustratively shown. A solid black plot 402 shows a normal state of the optical fiber signal. A dashed plot 404 shows a trigger state of the optical fiber signal after a button press. The change in curvature between the 'Normal' and 'Button Press' states of the fiber can easily be recognized. In an experimental setup, the fiber was integrated within a flexible metal tube that was itself integrated within a handheld pointing device device. The path of the fiber inside the pointing device passes through a spring-returned sliding mechanism (or 'button'). Depressing the button causes the sliding mechanism to translate in the direction of the press and the fiber undergoes a local deformation. Releasing the button causes the button to return to its original position, and the mechanism pulls the fiber back into a straight configuration. The metal tube is clamped distally to the translating mechanism so that the fiber tip does not translate during button presses. The solid black plot 402 shows low curvature during the normal setting, and the dashed plot 404 shows spikes in curvature during the button press.

Figure 6:
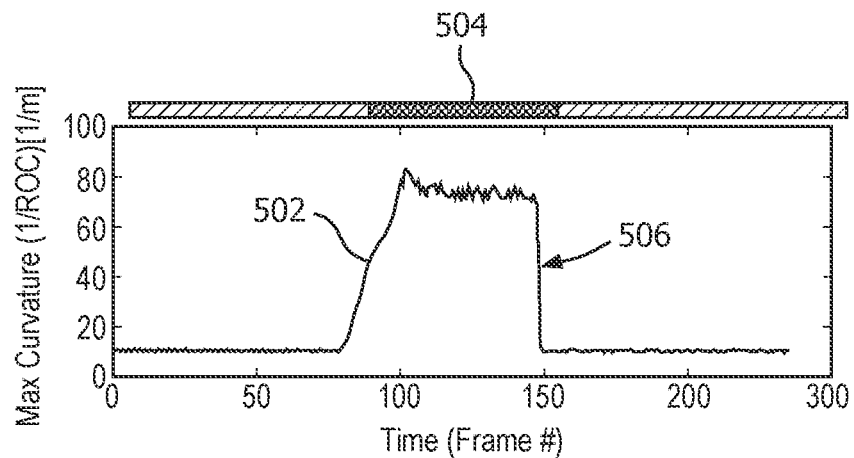
FIG. 6 is a graph showing maximum curvature (1/m) versus time (frame number) showing a difference between a normal state and a triggered state using an optical fiber in accordance with one embodiment.

Referring to FIG. 6, a graph of maximum curvature (1/radius of curvature) (1/m) versus time (in frames number) is shown measured in a section of the shape sensing fiber. By using a threshold of 40 $m^{-1}$, for example, the maximum curvature can be used to identify when a button is depressed. A maximum curvature plot 502 over time shows a period of 'Button Press' by a bar 504 corresponding to a plateau 506 in the maximum curvature plot 502, correlating to an increase in max curvature.

In this configuration, it is most likely that the fiber will be free floating within a lumen that is deformed. This permits the fiber to take up any path length changes due to the changes in curvature by translating within the lumen. This allows a proximal side to slide, in which case, a tip of the fiber still remains in a known position. Alternatively, a calibration can be performed to account and compensate for any translation of the tip during a button press. The example shown in FIG. 4C also addresses this because the curvature is always present along the fiber. The curvature simply changes its position.

In other embodiments, the shape sensing optical fiber 126 may undergo temperature change (or axial strain). Shape sensing optical fiber 126 may be fabricated with a quartz core and cladding with a protective coating (of acrylate, for example). Change in temperature will cause the quartz to expand and contract, leading to changes in strain. In optical shape sensing, this effect is normalized to properly reconstruct the shape of the shape sensing optical fiber 126. One way that this can be done is through the use of a normalizing central core that is placed at or close to the center of the fiber. If the core is exactly along the central axis of the fiber, it does not change length due to shape changes, and is principally affected by changes in length of the fiber due to tension or temperature.

Figure 7A:
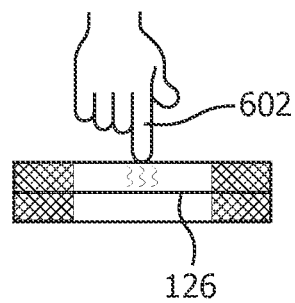
FIG. 7A is a cross-sectional view of a triggering device showing an untriggered and a triggered state activated by body temperature or other temperature change in accordance with one embodiment.
Figure 7B:
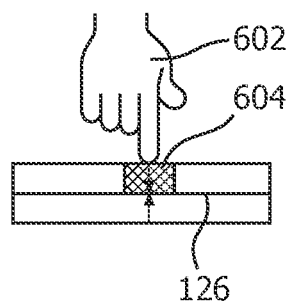
FIG. 7B is a cross-sectional view of a triggering device showing an untriggered and a triggered state using a pinching piece to apply pressure to an optical fiber in accordance with one embodiment.

Referring to FIGS. 7A and 7B, a shape sensing optical fiber 126 is configured to be activated (changed) using temperature or tension applied to the shape sensing optical fiber 126. Strain signals can be used as user inputs. In FIG. 7A, applying a finger 602 to the shape sensing optical fiber 126 can cause an increase in temperature. In FIG. 7B, tension can be applied to the shape sensing optical fiber 126 using a pinching piece 604 that is pushed into contact with the fiber by the user. In both cases, a change in axial strain is measured across the shape sensing optical fiber 126 that can be measured, for example, by the central core.

Figure 8:
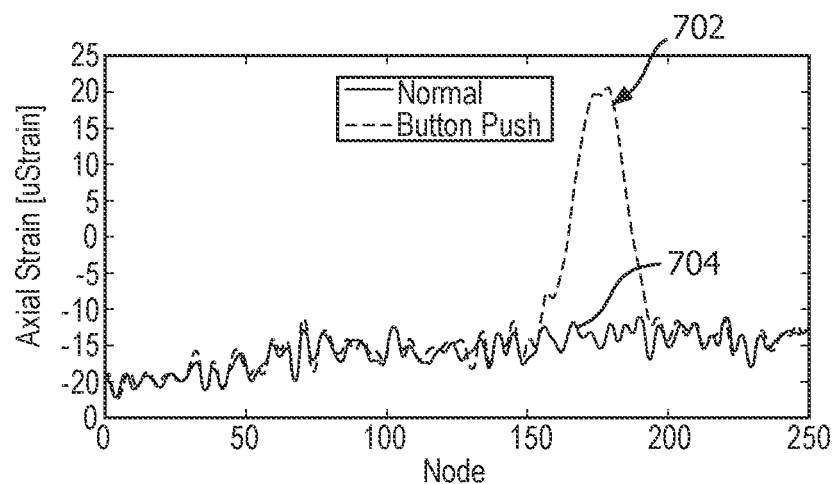
FIG. 8 is a graph showing axial strain (microstrain) versus node number depicting a difference between a normal state and a thermally triggered state using an optical fiber in accordance with one embodiment.

Referring to FIG. 8, a graph of axial strain (microstrain) versus node number along a fiber shows how axial strain increases in a region 702 where a finger transfers heat to the fiber. The expansion due to that heating causes an increase in axial strain that can be differentiated from a normal state 704. The change in axial strain caused by applying a warm finger may be employed as a trigger. Low axial strain during the normal state (704) increases in region 702 in axial strain due to the change in temperature during a finger press.

Figure 9:
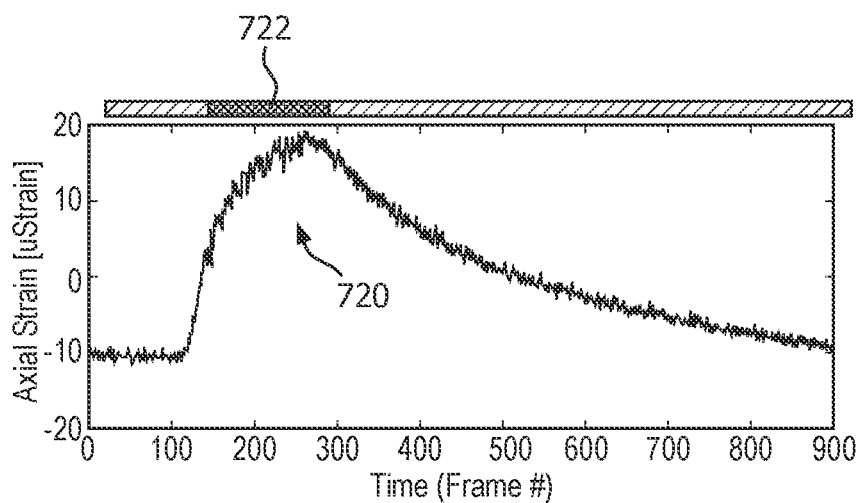
FIG. 9 is a graph showing axial strain (microstrain) versus time (frame number) depicting a response to a temperature change in an optical fiber in accordance with one embodiment.

Referring to FIG. 9, a graph shows maximum axial strain (microstrain) over time (based on number of frames) depicting a period 720 of a button press. A bar 722, correlating to an increase in maximum axial strain, indicates the duration of the button press. The nine hundred frames in FIG. 9 roughly correlate to 30 seconds of data acquisition. The graph shows how the maximum axial strain measured in the relevant section of fiber increases during contact with the warm finger, and that it slowly recovers (over ~20 seconds) to normal values after the contact is ended. This slow recovery could be a feature that prevents too short a time interval in between button clicks. The slow delay time constant is not expected in the case of tension shown in other embodiments.

Temperature change may also be employed as a safety feature. For example, a tool may only turn on when it knows the operator is holding it. It can be used in conjunction with another trigger, such as a curvature-inducing button press, to only permit that button press to happen when it also has a thermal signature. In this way, accidental triggering by dropping instruments or bumping them against other surfaces can be avoided.

Figure 10:
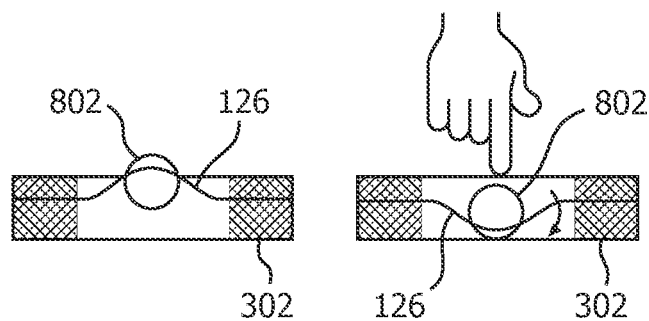
FIG. 10 is a cross-sectional view of a triggering device showing a normal state and a triggered state using a shape template in accordance with one embodiment.

Referring to FIG. 10, a shape sensing optical fiber 126 is configured to use activation in the form of a shape change applied to the shape sensing optical fiber 126. In such an embodiment, the use of the shape itself is employed as a trigger for user input. A button or other object (a shape template) 802 may be coupled to the shape sensing optical fiber 126. The change in orientation of the shape template 802 through a press, rotation, twist, translation, etc. can be used as an input. The shape template 802 could be employed as a button press, a rotary dial, a lever, a slide or any other similar type of input device.

Figure 11:
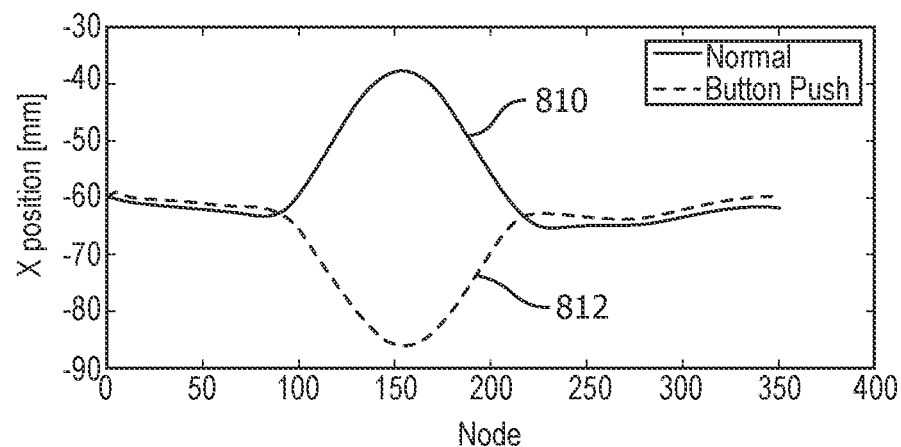
FIG. 11 is a graph showing x position (mm) versus node number depicting a difference between a normal state and a triggered state using an optical fiber triggered with a shape template in accordance with one embodiment.

Referring to FIG. 11, a graph of x position (mm) versus node number along a fiber shows a change in shape caused by rotating a fiber trigger. A plot 810 shows the x position of the shape during a normal setting, and a plot 812 shows a change in position during a button press. A difference in curvature occurs between the normal state in plot 810 and the button push state in plot 812 due to the change of shape through a rotating shape template.

Figure 12:
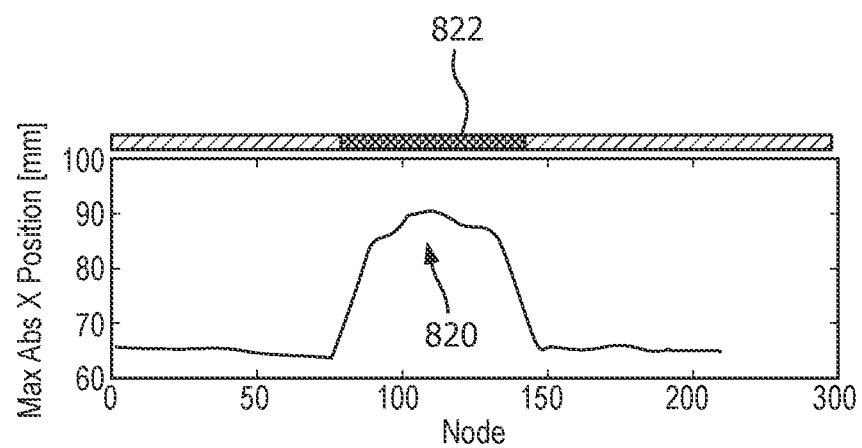
FIG. 12 is a graph showing maximum absolute x position (mm) versus node number depicting a response to a shape change in an optical fiber in accordance with one embodiment.

Referring to FIG. 12, a graph showing maximum absolute x position (mm) versus node number along a fiber depicts a period 820 of a button press. A bar 822, correlating to a change in maximum x position along the fiber, indicates the duration of the button press. The profile over time, using only the maximum absolute x-position, indicates a sharp rise and decline in the signal amplitude. This information can also be extracted in other ways, for example, by using a vector representation of the shape. Alternatively, the twist through the fiber could also be used for a similar function. In this case, the fiber can be free floating within a lumen, or fixed. The advantage of free floating implementation is that there is no accumulation of twist during rotation of the shape template. That may be of significance in a dial or rotary implementation.

Figure 13:
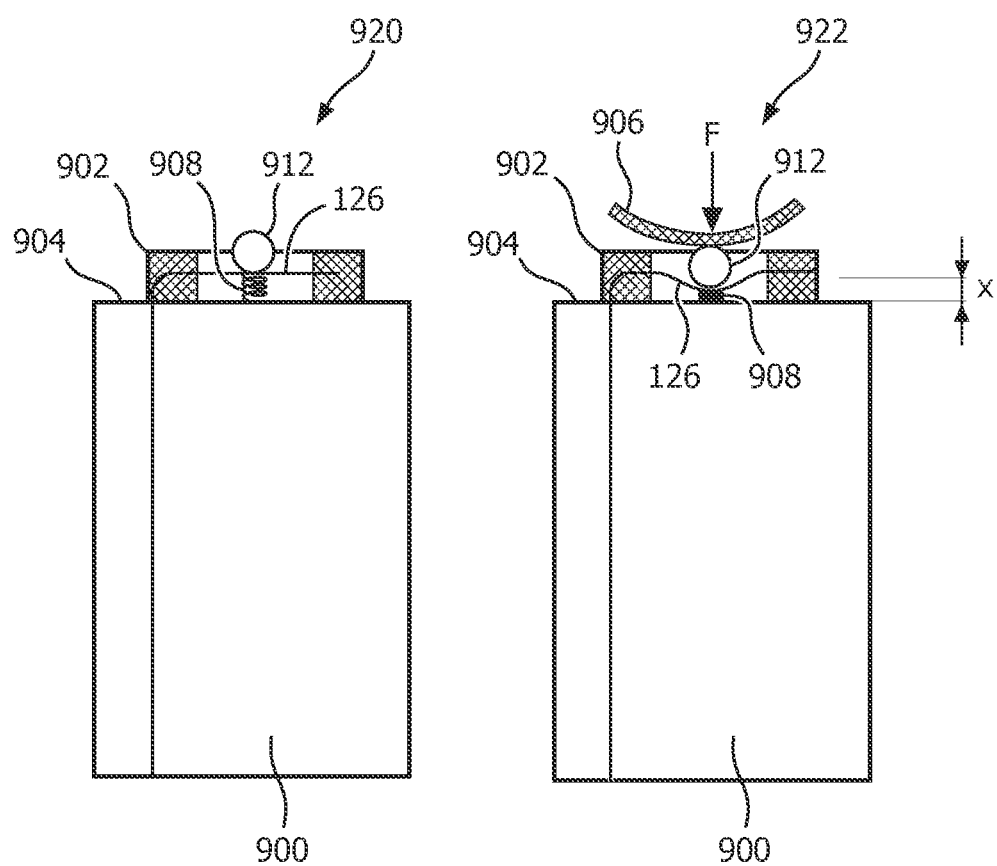
FIG. 13 shows cross-sectional views of a triggering device showing a normal state and a triggered state using a button for force sensing in accordance with one embodiment.

Referring to FIG. 13, force sensing can be provided in a similar manner as the change in shape sensing parameters, and can be employed as user input. A normal state 920 may include a biased mechanical element 912 (e.g., a button, soft portion or the like). A triggered state 922 may include the biased mechanical element 912 deflected to sense a contact force.

Force sensing can also be used to infer information about forces acting upon a device, such as a medical device or the like. Through integration into a device 900, components 902 of the device 900 can, for example, push on a part of the shape sensing optical fiber 126, causing a calibrated deformation in shape or curvature. Much in the same way that the button press is sensed as an on-off type of input, a similar concept can be applied to forces acting upon, for example, device 900 (a medical instrument). A tip or a portion 904 of the instrument uses a similar feature to what was previously described for the button press, but is now used to sense contact or forces F between the device 900 and another surface 906. Based on the selection of an appropriate spring constant, k, of a spring 908, the contact force F can be estimated from, e.g.: F=kx, where represents the compression of the spring as measured by the shape sensing optical fiber 126.

The example described in FIG. 13 can also be extended to more than just one dimensional force sensing through the manipulation of the shape sensing optical fiber 126 and an appropriate mechanical structure 902 within or on the device 900. In addition, the example provides a discrete force measurement. Having an array of springs all connected to the fiber would permit for a force distribution map to be created using the same principal. Similarly, torque measurements can be performed based on this information. This can also extend along the shape sensing optical fiber 126 to other nodes of the shape sensing optical fiber 126.

The present principles apply to any use of an shape sensing optical fiber as a trigger in devices. The present principles are particularly relevant to medical application such as, orthopedic navigation including knee replacement, anterior cruciate ligament (ACL) repair, hip replacement, brain surgery, and other such applications and are also relevant to provide user triggering for any medical device or the like. The shape sensing optical fibers described apply to Rayleigh (enhanced and regular) as well as Fiber Bragg implementations of shape sensing fiber.

Figure 14:
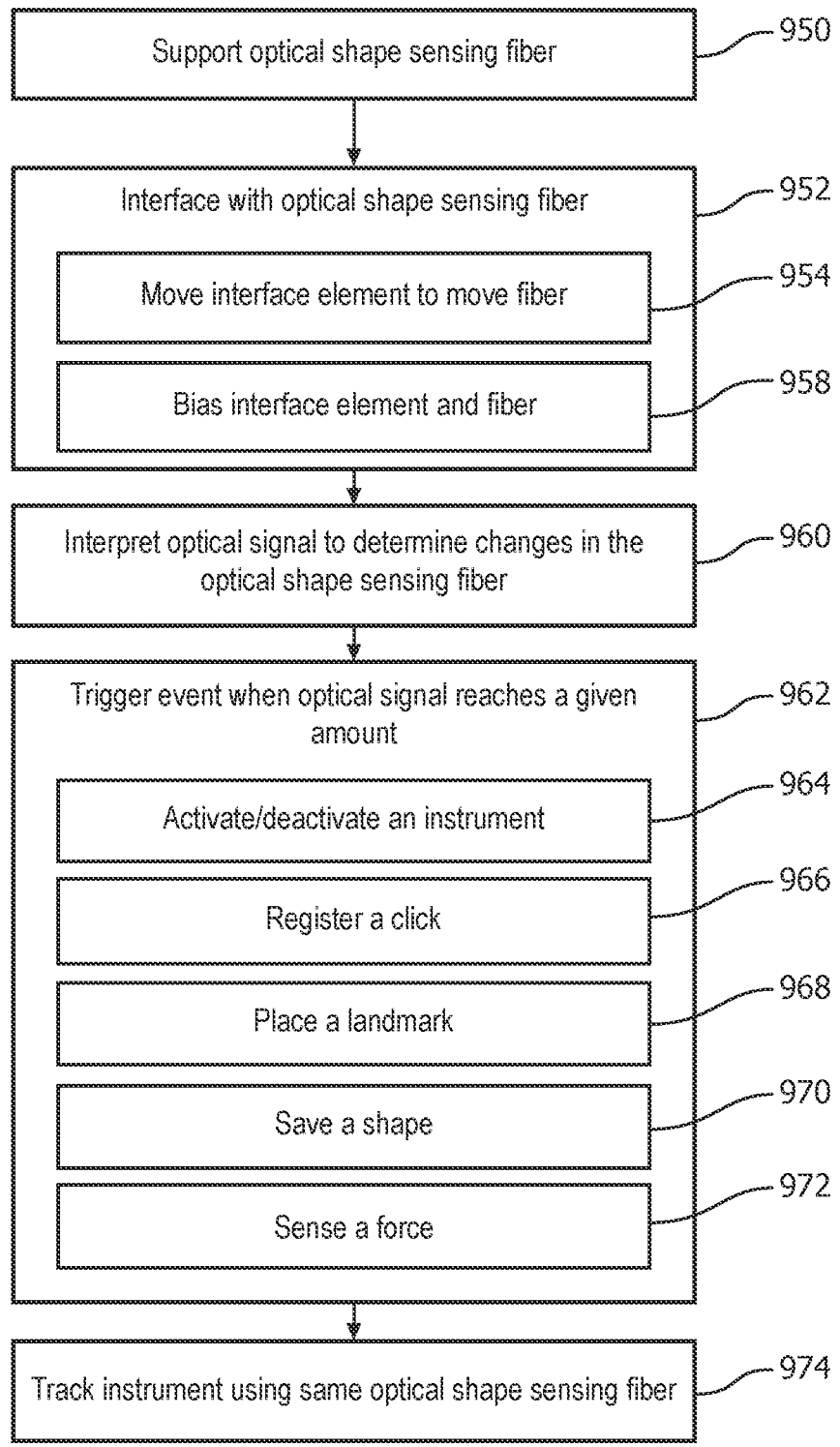
FIG. 14 is a flow diagram showing a trigger method using an optical shape sensing fiber in accordance with illustrative embodiments.

Referring to FIG. 14, a method for triggering an event is shown in accordance with the present principles. In block 950, at least a portion of a shape sensing optical fiber is supported in a supporting device. The supporting device may include a medical instrument or may include any base configured to support an optical fiber or fibers configured for shape sensing. In block 952, the shape sensing optical fiber is interfaced within the supporting device (e.g., using an interface element) to cause a change in a property of the fiber. The change in property of the fiber may include a change in axial strain or a shape change. The shape changes may be provided due to at least one of a position change, a twist, an orientation change, a bend, etc. The change in axial strain in the shape sensing optical fiber may be due to a temperature difference, e.g., body temperature, tension, etc. Combinations of these are also contemplated.

In block 954, the interface element may include a mechanical element, body part or soft region on a device carrying the fiber. The mechanical element, body part or soft region may be employed to move the shape sensing optical fiber. The interface element may be employed to translate a deflection along a length of the shape sensing optical fiber.

For example, slider buttons, knobs, hubs or other elements may be employed. In block 958, the interface element may include a biased interface element. The interface element is biased with the shape sensing optical fiber to a normal state. The bias may be provided by a spring, using resilient material properties, etc. In block 960, an optical signal received from the shape sensing optical fiber is interpreted to determine the changes in the property of the shape sensing optical fiber.

In block 962, an event is triggered when a property changes by a given amount. The amount may include a user set threshold. The threshold may include an axial strain value, a radius of curvature, a particular orientation of the fiber, a force applied, a temperature measured, a correlation with an expected shape or curvature profile, etc. In block 964, triggering an event may include activating or deactivating an instrument. In block 966, triggering an event may include registering a click upon changing a curvature of the shape sensing optical fiber. This is similar to a mouse click, but employing shape sensing. In block 968, triggering an event may include placing or recording a landmark on a subject upon changing a curvature of the shape sensing optical fiber. This may include the use of a pointing device device. When the pointing device is in position, the user presses a button, etc. to induce a shape change in the fiber and stores the position(s) of the pointing device. In block 970, triggering an event may include saving a shape of a medical device upon changing a curvature of the shape sensing optical fiber. In this case, the fiber may be coupled with a catheter or other device. Upon achieving a certain position of the catheter, it may be desirable to store that position of the catheter. The user may induce a kink in the catheter at a predetermined position to trigger the event of storing the shape of the catheter in memory. This may include using the fingers of the user, or the catheter may include a soft interface element to permit the triggering. In block 972, triggering an event may include sensing a force upon changing a curvature or axial strain of the shape sensing optical fiber.

Other triggered event and configurations are also contemplated. In block 974, a medical instrument or other device may be tracked by shape sensing optical using the same shape sensing optical fiber.

The device, system and method of the present invention may be used advantageously with longitudinal encoding.

Longitudinal Encoding for Registration

When two devices such as a shape-sensed guidewire and a catheter are concentric, the shape information about one device can be used with respect to the other device. A key registration necessary for this use is the longitudinal translation between the two devices. This registration can be performed by using a known shape deformation of the sensed device at a specific location along the unsensed device. The shape deformation can be detected through curvature detection, axial strain (from heating or tensions) or 2D or 3D shape matching.

Applicant's prior, co-pending application entitled "Device Tracking using Longitudinal Encoders", WO2015049142, published Apr. 9, 2015, broadly describes a method for this longitudinal encoding and is incorporated in its entirely by reference herein and made a part of this specification.

Hub designs.

Figures 15A, 15B:
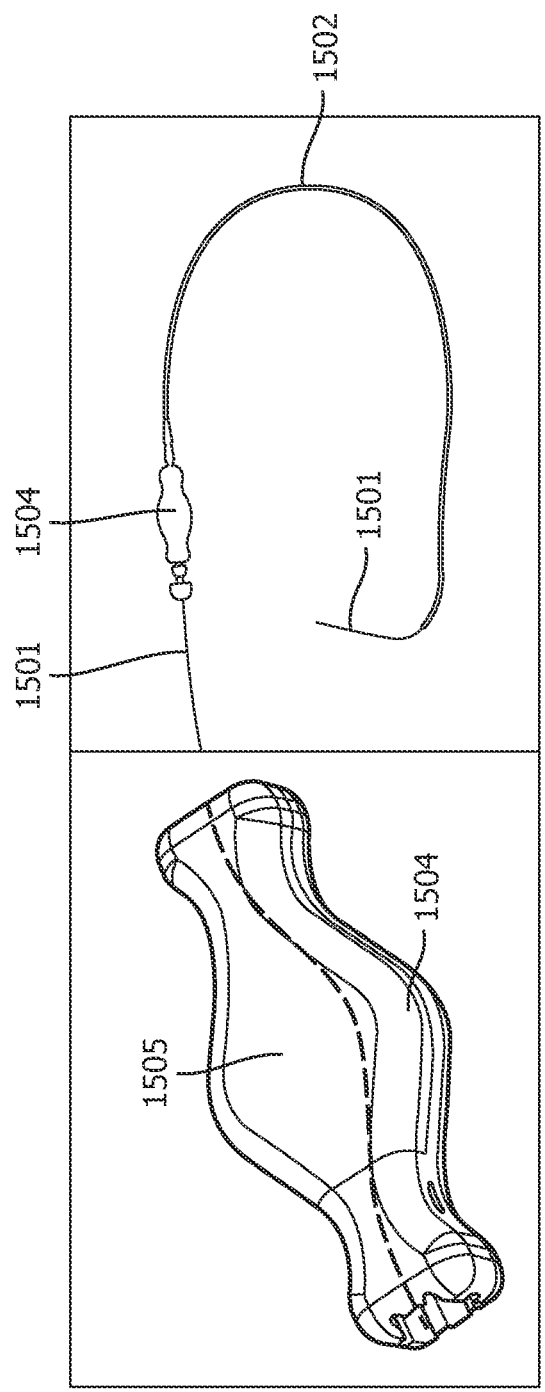
FIG. 15A is a view of a locking hub that deforms a guidewire lumen into a known shape.
FIG. 15B is a view of a hub, guidewire and catheter showing the guidewire passing through a lumen into the catheter.

A triggering device in accordance with the present invention can be incorporated into a movable or stationary fitting or "hub", which may or may not also be an interface element, such as the hub 1504 with lumen 1505 shown in FIG. 15A, which forms a guidewire lumen into a known shape or curvature. Many different versions of hub designs are possible. In FIG. 15B the guidewire 1501 is shown passing through a hub 1504 (including lumen 1505) through catheter 1502.

User input using optical shape sensing.

As explained above, an shape sensing optical fiber can be used as a trigger to provide user input to a computer if the fiber is already embedded or attached to a medical instrument for tracking the shape or position or the instrument. This user input can, for example, be detected in any or all of three ways: (1) identifying a change in curvature at a defined location along the sensor, (2) matching a specific shape or pattern made with the sensor at a location along the sensor or (3) looking for a change in axial strain or temperature at a location along the sensor.

Referring to FIGS. 4 A, B, C and the discussion of these Figures earlier in this specification, a fiber can be configured to generate a change in curvature when a button is pressed. This button can be placed anywhere along the shape sensing fiber after a launch point. A similar approach can be used to measure changes in the actual shape of the fiber as it bends in response to the button being pressed.

A shape sensed fiber may be configured to change in curvature during a button press, as shown in FIG. 4A. Also, as shown in FIG. 4B, the fiber can be spring-loaded in order to be sure that it returns to its normal position when not being pressed.

Referring again to FIG. 7A, B, axial strain or temperature changes can be used to generate user input. A finger 602 in FIG. 7A can be applied to the shape sensing optical fiber 126 to cause in increase in temperature. Tension can be applied as shown in FIG. 7B to the shape sensing optical fiber 126 using a pinching piece 604 that is pushed into contact with the fiber by the user. In both cases a change in axial strain is measured across the fiber that can be measured by, for example, the central core of the fiber.

Figure 16:
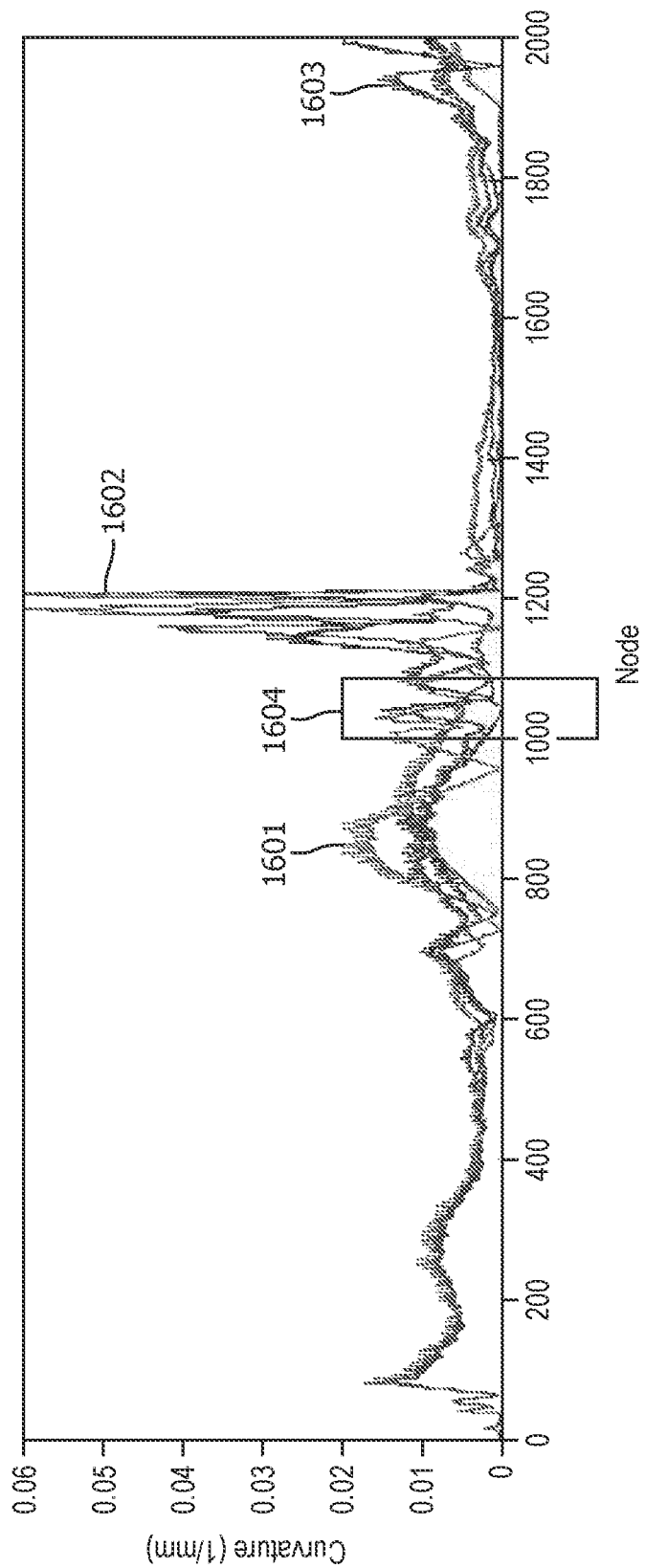
FIG. 16 is a graph showing curvature for three shape sensing measurements.during navigation.

Referring to FIG. 16, a curvature plot is shown for three shape sensing measurements during navigation. The three shapes 1601, 1602, 1603 are taken over a period of time during typical guidewire navigation. It can be seen that picking out a specific change in curvature without limiting the search range is challenging. There is a significant change in curvature along the fiber, which may make it difficult or impossible to know which of those curvature changes represent a 'trigger' and which of them represent normal curvature during navigation. Narrowing this curvature to find a trigger is done by focusing on a specific segment of the optical signal curvature or shape data, such as the box 1604.

For a change in curvature or shape in a certain region of the fiber to be used as an input or trigger to the system software, for example, the optical sensing module 115, an algorithm is used to monitor a specific region of the fiber. This monitoring is practicable in some cases, for example, in circumstances in which the fiber is integrated into a device such as a catheter. In other cases, however, a trigger region in the fiber may not be fixed. For example, if it is desired to enable a clicker that can slide overtop of a guidewire then a way is needed to restrict the search region to only the region of a hub or similar fixture in order to identify a trigger. Otherwise, there may be so much change in curvature along the entire fiber during use that it may be impossible or very difficult to pick out the trigger from that signal.

Using a hub template to only search within that template for a triggering curvature signal.

Some designs for hubs or similar fixtures may allow tracking location along a length of the fiber. A system can then determine precisely where to search for user input, allowing for the addition of interface elements such as buttons or other user input devices to the hub or other fixture.

If the user input is in the form of changes in temperature or axial strain, the design may be relatively simple. Any number of buttons or other user input mechanisms can be added to the hub or other fixture, and the software application can search for user input within the template area, even as a template slides along the shape sensing optical fiber. Because the temperature/axial strain input does not affect the curvature of the template in any significant way, a template within a hub or other fixture requires no changes in design to accommodate these added inputs, and the software will still be able to locate the distinguishing curvature or other spatial relationship of the template.

If the user input is in the form of changes to the curvature of the fiber, the template design must be modified. Software (e.g. of the optical sensing module 115, locates the hub template by searching for its distinctive curvature. If, however, a button or other user interface mechanism is used that changes the template curvature, the software will no longer be able to detect the hub template location. To accommodate this, the template can be subdivided into separate sections so that user input can be sensed in the areas not covered by the template search algorithm. In essence, the software will search for two or more templates at fixed distances from one another instead of just one template, as in FIG. 17. The user input can now be tracked in a location that moves along with the hub.

A similar concept can be used more generally to search for specific features along the fiber. In the above example, the template was used to restrict the search for user input. More generally, because the template within the hub can be tracked as the fiber slides through the hub, the matched template location can be used to restrict the search for other desired features.

Figure 17:
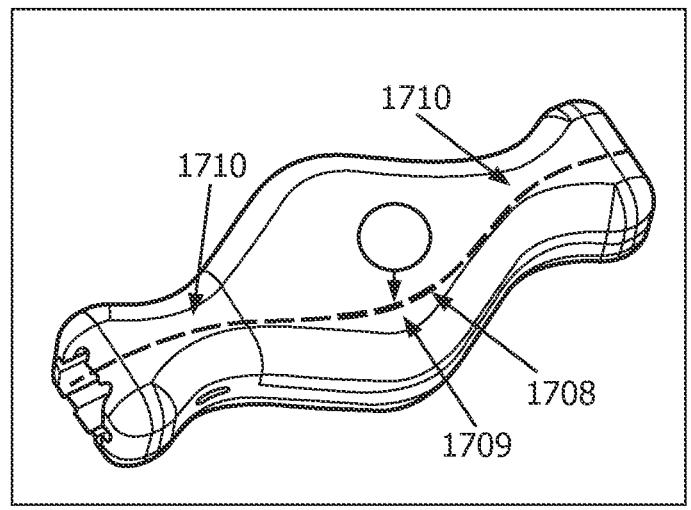
FIG. 17 is a view of a modified hub that deforms a guidewire lumen into a known shape.

FIG. 17 provides an example of a modified hub that deforms the guidewire lumen 1708 into a known shape. The template tracking algorithm runs on only sections of the deformation such as the user input search area 1709 in a hub template tracking area 1710 shown in FIG. 17, allowing for the user input (ex: button) in another section of the deformation. This sub-sectioning can be repeated multiple times to allow for multiple user input areas.

Using an anatomical template to select a portion of the shape.

Figures 18A, 18B:
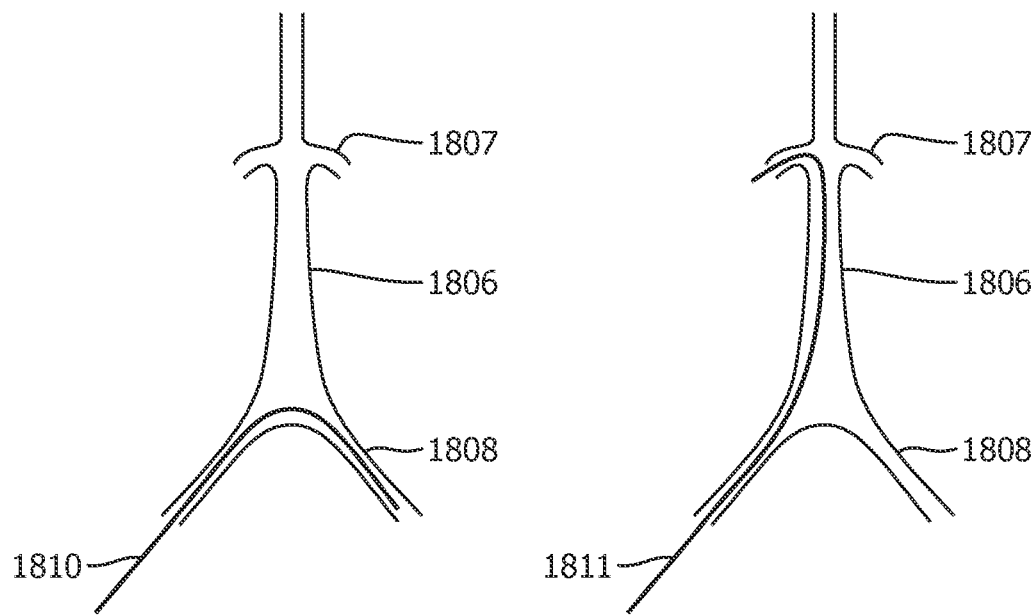
FIG. 18A,B is a diagram of different shapes that can be used as templates for an anatomical position.
Figure 19:
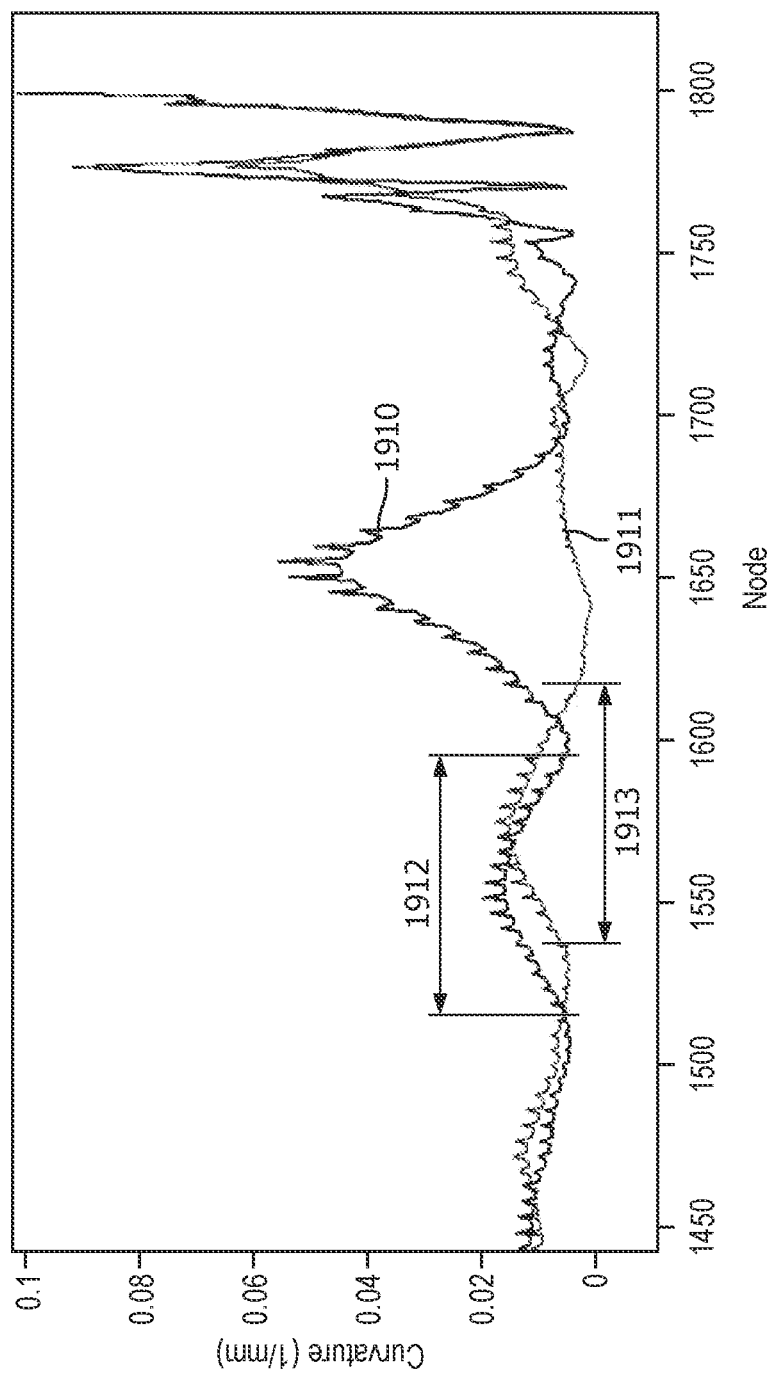
FIG. 19 is a graph of pre-clinical curvature data showing the difference in curvature betweenan iliac crossover and cannulation of the right renal artery.

FIG. 18A,B outlines an abdominal aorta 1806, renal arteries 1807 and iliac arteries 1808 and provides an example of two common guidewire positions during vascular navigation from a femoral incision. These two positions have quite different shapes and curvature profiles (as shown in FIG. 19). A guidewire 1810 following an iliac crossover is shown in FIG. 18A. A guidewire 1811 following a cannulation of a renal artery 1807 is shown in FIG. 18B.

A template curvature profile for an 'iliac crossover' as in FIG. 18A can be created. That template can then be run on the live curvature data to detect if an iliac crossover has occurred. Once that has been detected, knowledge of where that template occurred along the fiber can be used to segment only a portion of the fiber that is past a bifurcation. This segment can then be used for (for example): registration to live imaging, device identification, visualization (for example, zooming in the visualization onto that portion of the fiber), providing feedback to an operator as to the guidewire's being across the iliac arteries, providing feedback in the form of a measured distance along the device beyond the crossover point as well as to eliminate contribution of a particular section from consideration as a user input (e.g. as one that can only be performed outside the body). Feedback may be unnecessary when a shape is overlayed on a pre-operative or intraoperative image, but when such an image is not available (for example, in feeding tube placement) feedback becomes a valuable tool.

The template curvature can be derived from a variety of sources such as:
  A general template for a specific anatomy that is not patient-specific.
  A patient-specific template derived from: (1) CT, x-ray or other pre-operative or intraoperative imaging of the vascular structure, or (2) a shape sensed device (either the same one currently in use, or a different one) that previously performed that positioning.
  An adaptive algorithm that searches for potentially meaningful curvature templates and then prompts the operator to confirm. It thus becomes 'trained' as it is used.
  User input to draw a template shape (perhaps overlayed on a pre-op CT).
  Detecting a template to segment the shape into in-body and out-of-body segments.

In FIG. 19 plots of pre-clinical curvature data show the difference in curvature between the iliac crossover 2010 and the cannulation of the right renal artery 2011.

In FIG. 19 another shape appears in both plots, but that shape (template) is translated slightly (from the shape 1912 at a peak at node 1550 in the iliac crossover 1910 to the shape 1913 at a peak at node 1575 in the renal cannulation 1911. This implies that both positions (iliac crossover and renal cannulation) experienced the same curve, but the renal cannulation 1911 shape experienced it at a later point in the fiber. In this case, the shape actually represents the introducer sheath which brings the devices into the body. Thus, by using a template to detect this shape along the fiber, it is possible to identify where each device enters the body. Here it is seen that since the introducer template curvature appears later in the renal cannulation 1911 sensor data, that sensor has less length inside the body. This information can be quite helpful in order to segment the shape into in-body and out-of-body portions. Then, if it is necessary to search for a user button press, the search can be limited to the portion of the shape that is out-of-body since it is known that the button will always stay outside the body.

All of these examples have used curvature as the shape component to use for a template. Any shape component can, however, be used, including twist, axial strain, 2D shape, 3D shape, etc.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for triggering with shape sensing optical fiber (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A triggering device, comprising:
   an optical fiber configured for optical shape sensing;
   a medical instrument or base configured to support at least a portion of the optical fiber;
   an interface element configured to generate a user input by directly interacting with the optical fiber associated with the medical instrument or base to cause a change in a property of the optical fiber, wherein the optical fiber functions as an input device;
   a processor; and
   a non-transitory computer readable medium, which stores instructions when executed by the processor causes the processor to interpret an optical signal to determine changes in the property of the optical fiber and accordingly generate a corresponding trigger signal.

2. The triggering device as recited in claim 1, wherein the interface element includes one of a mechanical element, a soft material or a body part.

3. The triggering device as recited in claim 1, wherein the interface element includes a button or slide configured to interact with the optical fiber.

4. The triggering device as recited in claim 1, further comprising a biasing button configured to restore the interface element and the optical fiber to a normal state.

5. The triggering device as recited in claim 1, wherein the change in the property includes a shape change in the optical fiber.

6. The triggering device as recited in claim 1, wherein the change in the property includes a change in axial strain in the optical fiber.

7. The triggering device as recited in claim 1, wherein the trigger signal is configured to activate or deactivate an instrument or software function.

8. The triggering device as recited in claim 1, wherein an event includes enabling a function of an instrument in accordance with a change in axial strain due to temperature.

9. The triggering device as recited in claim 1, further comprising a medical instrument including the optical fiber, the medical instrument being tracked by optical shape sensing of the optical fiber.

10. The triggering device as recited in claim 1, wherein the medical instrument or base and the interface element are configured to function as a force sensor based on a change in the optical fiber.

11. A triggering system, comprising:
    one or more optical fibers configured for optical shape sensing;
    a medical instrument including the one or more optical fibers, the medical instrument being tracked by optical shape sensing, the medical instrument forming a supporting device configured to support at least a portion of the one or more optical fibers;
    an interface element configured to generate a user input by directly interacting with the one or more optical fibers in the supporting device to cause a change in a property of the one or more optical fibers, wherein the one or more optical fibers function as an input device;
    a processor; and
    a non-transitory computer readable medium, which stores instructions when executed by the processor causes the processor to interpret an optical signal to determine changes in the property of the optical fiber and accordingly generate a trigger signal if a threshold is reached.

12. The triggering system as recited in claim 11, wherein the interface element includes one of a mechanical element, a soft material or a body part.

13. The triggering system as recited in claim 11, wherein the interface element includes a button or slide configured to interact with the one or more optical fibers.

14. The triggering system as recited in claim 11, further comprising a biasing button configured to restore the interface element and the one or more optical fibers to a normal state.

15. The triggering system as recited in claim 11, wherein the change in the property includes a shape change in the one or more optical fibers.

16. The triggering system as recited in claim 11, wherein the change in the property includes a change in axial strain in the one or more optical fibers.

17. The triggering system as recited in claim 11, wherein the trigger signal is configured to activate or deactivate an instrument or software function.

18. The triggering system as recited in claim 11, wherein an event includes enabling a function of an instrument in accordance with a change in axial strain due to temperature.

19. The triggering system as recited in claim 11, further comprising a medical instrument including the one or more optical fibers, the medical instrument being tracked by optical shape sensing of the one or more optical fibers.

20. A method for triggering an event, comprising:
    supporting at least a portion of a shape sensing optical fiber in a supporting device;
    interfacing directly with the shape sensing optical fiber in the supporting device to generate user input by causing a change in a property of the optical fiber, wherein the optical fiber functions as a user input device;
    interpreting an optical signal to determine the change in the property of the optical fiber; and
    triggering an event when the change in the property reaches a threshold.

* * * * *